(12) United States Patent
Bogue

(10) Patent No.: US 11,129,799 B2
(45) Date of Patent: Sep. 28, 2021

(54) DUAL LANE COATING

(75) Inventor: Beuford A. Bogue, New Carlisle, IN (US)

(73) Assignee: Aquestive Therapeutics, Inc., Warren, NJ (US)

( * ) Notice: Subject to any disclaimer, the term of this patent is extended or adjusted under 35 U.S.C. 154(b) by 283 days.

(21) Appl. No.: 13/084,681

(22) Filed: Apr. 12, 2011

(65) Prior Publication Data

US 2012/0263865 A1  Oct. 18, 2012

(51) Int. Cl.
*C23C 14/54* (2006.01)
*A61K 9/70* (2006.01)

(52) U.S. Cl.
CPC ................. *A61K 9/7007* (2013.01)

(58) Field of Classification Search
CPC ............ A61K 9/54; C23C 14/54; C23C 16/52
USPC ..................... 427/8, 9; 118/16; 424/443, 439
See application file for complete search history.

(56) References Cited

U.S. PATENT DOCUMENTS

| | | | |
|---|---|---|---|
| 4,029,757 A * | 6/1977 | Mlodozeniec | A61J 3/00 156/204 |
| 5,858,545 A * | 1/1999 | Everaerts | C08F 290/148 428/447 |
| 5,948,430 A | 9/1999 | Zerbe et al. | |
| 6,177,096 B1 | 1/2001 | Zerbe et al. | |
| 6,284,264 B1 | 9/2001 | Zerbe et al. | |
| 6,592,887 B2 | 7/2003 | Zerbe et al. | |
| 6,709,671 B2 | 3/2004 | Zerbe et al. | |
| 7,357,891 B2 | 4/2008 | Yang et al. | |
| 7,425,292 B2 | 9/2008 | Yang et al. | |
| 7,666,337 B2 | 2/2010 | Yang et al. | |
| 7,749,417 B2 | 7/2010 | Schäfer et al. | |
| 7,824,588 B2 | 11/2010 | Yang et al. | |
| 7,897,080 B2 | 3/2011 | Yang et al. | |
| 8,291,798 B2 | 10/2012 | Schäfer et al. | |
| 8,865,202 B2 | 10/2014 | Zerbe et al. | |
| 8,956,685 B2 | 2/2015 | Bogue et al. | |
| 2001/0046511 A1 | 11/2001 | Zerbe et al. | |
| 2002/0182333 A1 * | 12/2002 | Seaver | B05B 5/0255 427/8 |
| 2004/0241294 A1 | 12/2004 | Barabolak et al. | |
| 2005/0037055 A1 | 2/2005 | Yang et al. | |
| 2008/0050422 A1 | 2/2008 | Myers et al. | |
| 2008/0260809 A1 * | 10/2008 | Yang | |
| 2008/0299197 A1 | 12/2008 | Toneguzzo et al. | |

(Continued)

FOREIGN PATENT DOCUMENTS

| | | |
|---|---|---|
| JP | 2001-504106 A | 3/2001 |
| JP | 2004-529781 A | 9/2004 |

(Continued)

OTHER PUBLICATIONS

International Search Report for PCT/US12/32342, dated Jul. 9, 2012.

(Continued)

*Primary Examiner* — Hai Y Zhang
(74) *Attorney, Agent, or Firm* — Hoffmann & Baron, LLP

(57) ABSTRACT

The present invention relates to methods and apparatuses for forming an active-containing film product, while significantly reducing the amount of wasted active material. The resulting product is an active-containing film product that meets the user's predetermined criteria of physical properties and is suitable for use.

15 Claims, 8 Drawing Sheets

(56) References Cited

U.S. PATENT DOCUMENTS

2010/0092545 A1    4/2010  Yang et al.
2012/0114705 A1    5/2012  Zerbe et al.

FOREIGN PATENT DOCUMENTS

JP    2010-504993   A    2/2010
WO        02/064123 A2   8/2002
WO     2008/039737  A2   4/2008

OTHER PUBLICATIONS

JP 2001-504106 A, English-language abstract for corresponding document: DE19646392 (A1); Machine Translation; U.S. Pat. No. 5,948,430 (previously submitted in the Information Disclosure Statement filed on Jul. 25, 2012); U.S. Pat. No. 6,177,096 B1; U.S. Pat. No. 6,284,264 B1; U.S. Pat. No. 6,592,887 B2; U.S. Pat. No. 6,709,671 B2; U.S. Pat. No. 8,865,202 B2; U.S. 2001/0046511 A1 and U.S. 2012/0114705 A1.
JP 2004-529781 A, English-language abstract for corresponding document: WO02064123 (A2); Machine Translation; WO 02/064123 A2; U.S. Pat. No. 7,749,417 B2; U.S. Pat. No. 8,291,798 B2.
JP 2010-504993 A, English-language abstract for corresponding document: U.S. 2008050422 (A1); Machine Translation; WO 2008/039737 A2; U.S. 2008/0050422 A1.

* cited by examiner

DUAL LANE COATING

FIELD OF THE INVENTION

The present invention relates to methods and apparatuses for forming an active-containing film product, while significantly reducing the amount of wasted active material. The resulting product is an active-containing film product that meets the user's predetermined criteria of physical properties and is suitable for use.

BACKGROUND OF THE INVENTION

The use of dissolvable or disintegrable films for the administration of therapeutic active agents, such as pharmaceuticals, bioeffective agents, cosmetic agents, and other similar materials, is becoming increasingly popular. Delivery through such films has a considerably high number of benefits, including, for example, ease of administration to the user. Such films should have a fairly uniform size, and a substantially uniform distribution of components per each unit of dosage. The substantially uniform distribution of components is quite important when the films include pharmaceutical components, to ensure accurate dosages.

Films may be formed in any desired fashion, and in some cases it may be useful to form a large-scale batch of film products at the same time and then subsequently size and cut individual dosage units from the film. Typically, a wet film-forming matrix is deposited onto the surface of a substrate, and then dried to form the resulting film, which is then sized and cut into individual film strip products. Unfortunately, however, such typical processes require several adjustments to achieve the desired coat weight and moisture level in the resulting film. During these adjustment periods, the film that is generated is considered wasted film and must be discarded. This adjustment period therefore results in a great deal of wasted film.

Actives used in such films may be quite expensive, particularly if such actives include pharmaceuticals or other bioeffective agents. If the film being formed during the adjustment period includes active materials, this wasted material may be extremely costly to the company.

As such, the present invention seeks to solve the problem of wasted active during the early stages of a film forming process. Films formed by the present invention may save not only wasted active materials but also save a considerable amount of wasted expense.

SUMMARY OF THE INVENTION

In one embodiment of the present invention, there is provided a method of forming an active-containing film product in a film forming apparatus, including the steps of: (a) providing a coating head capable of depositing a wet film product in a first lane and in a second lane parallel with the first lane; (b) providing a first batch of a film forming matrix including at least one polymer; (c) providing a second batch of a film forming matrix including at least one polymer and an active component; (d) applying a layer of the first batch with the first lane and drying the first applied layer to form a resulting surrogate film; (e) measuring the resulting surrogate film for at least one physical property and determining whether the at least one physical property meets predetermined criteria; (f) optionally, adjusting at least one processing parameter and repeating steps (d) and (e) above; and (g) applying a layer of the second batch with the second lane and drying the second applied layer to form an active-containing resulting film.

The present invention may further provide a film forming apparatus for forming an active-containing film product including: (a) a movable substrate; (b) a coating head capable of depositing a wet film product in a first lane and in a second lane substantially parallel to the first lane, (c) a drying apparatus sized to accommodate the substrate; (d) an apparatus to feed a first batch of film forming material to the first lane; and (e) an apparatus to feed a second batch of film forming material to the second lane.

DETAILED DESCRIPTION OF THE INVENTION

Figure 1A:
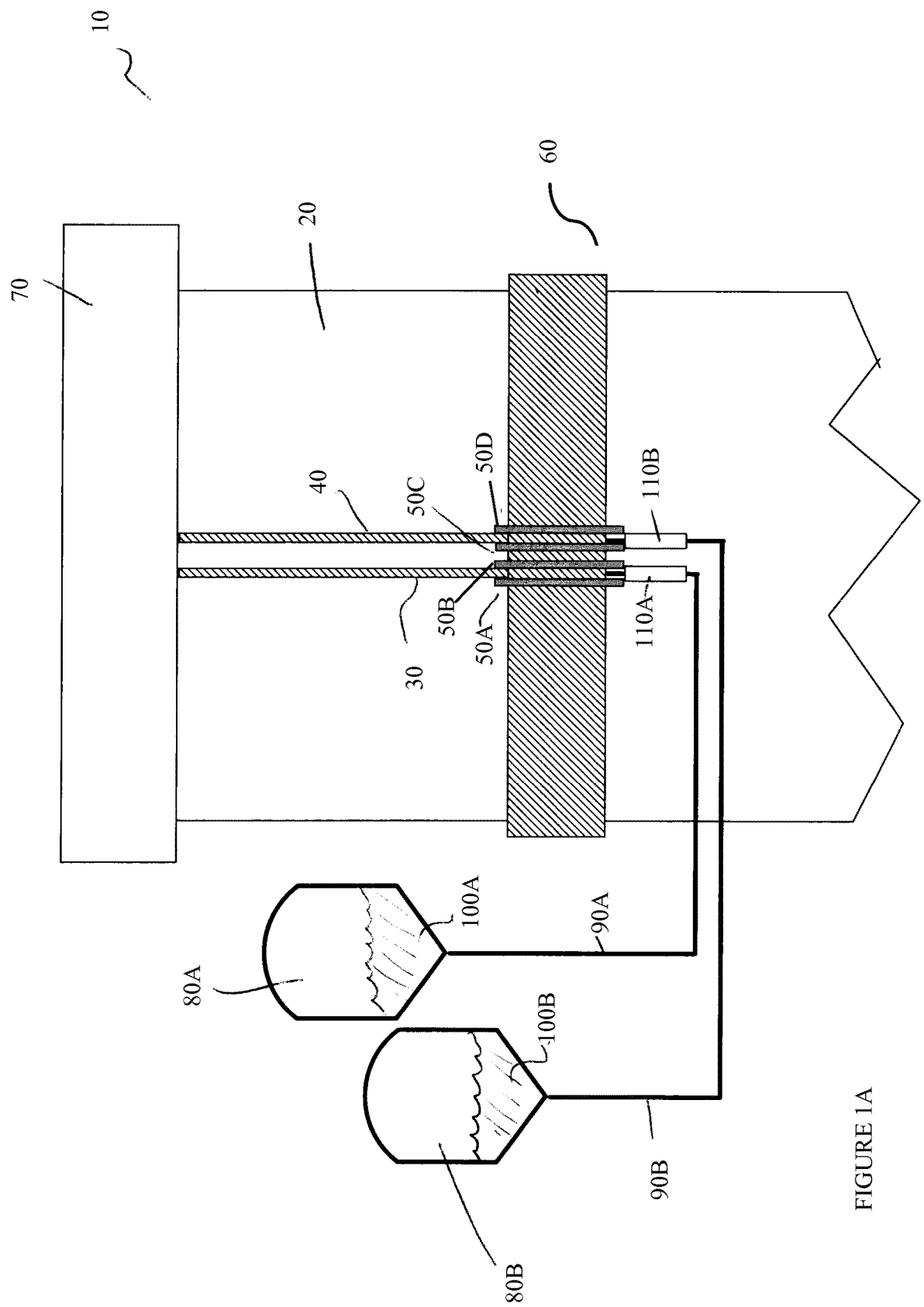
FIGS. 1A-1B depict an apparatus useful in the present invention, where two lanes of film are formed using a coating roller system.
Figure 1B:
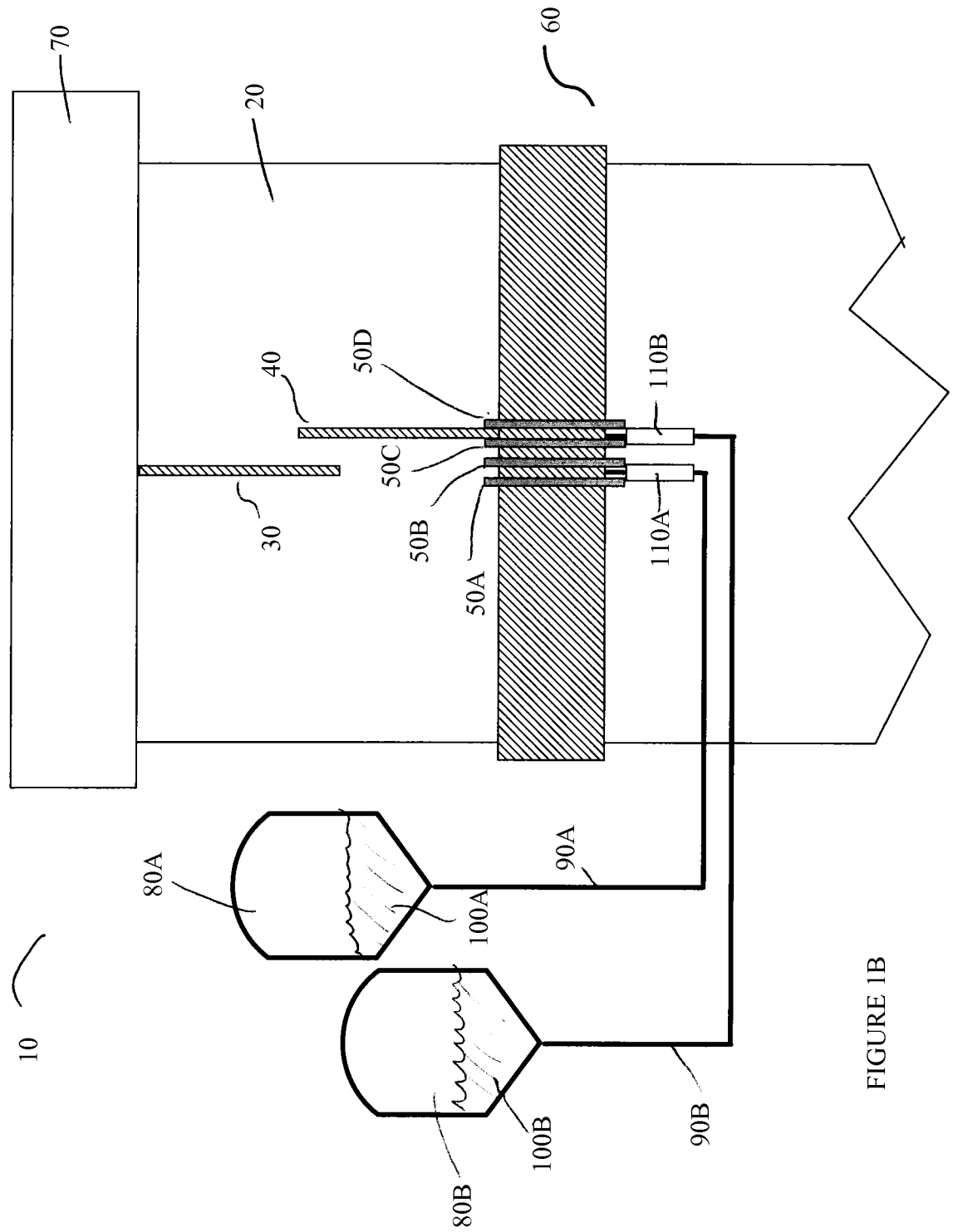

The present invention relates to methods and apparatuses designed for forming film products, including film products that include at least one active composition. Specifically, the invention provides a method and apparatus for forming film products that minimizes the amount of wasted active materials typically required in small batch size film processing. Film systems embody a field of technology that has major advantages in areas of administering drug, medicament, and various other active and agent delivery systems to an individual in need thereof. In order to provide a desirable final product that exhibits advantageous characteristics and desirable properties, including uniformity of content, the processing and manufacturing of film products and film technology is technologically demanding and cumbersome.

As used herein, the terms "pharmaceutical", "medicament", "drug" and "active" may be used interchangeably, and refer to a substance or composition useful for the prevention or treatment of a condition. The terms may include pharmaceuticals, neutraceuticals, cosmetic agents, biologic agents, bioeffective substances, and the like.

It will be understood that the term "film" includes delivery systems of any thickness, including films and film strips, sheets, discs, wafers, and the like, in any shape, including rectangular, square, or other desired shape. The film may be in the form of a continuous roll of film or may be sized to a desired length and width. The films described herein may be any desired thickness and size suitable for the intended use. For example, a film of the present invention may be sized such that it may be placed into the oral cavity of the user. Other films may be sized for application to the skin of the user, i.e., a topical use. For example, some films may have a relatively thin thickness of from about 0.1 to about 10 mils, while others may have a somewhat thicker thickness of from about 10 to about 30 mils. For some films, especially those intended for topical use, the thickness may be even larger, i.e., greater than about 30 mils. In addition, the term "film" includes single-layer compositions as well as multi-layer compositions, such as laminated films, coatings on films and the like. The composition in its dried film form maintains a uniform distribution of components through the processing of the film. Films may include a pouch or region of medicament between two films.

The term "patch" as used herein is intended to include multi-layered film products, where the first layer (or "backing layer") is a film product that has a slower rate of dissolution than the second layer (or "active layer"). Patches described herein generally include the first and second layers adhered or laminated to each other, where the second layer has a smaller length and/or width of the first layer, such that at least a portion of the surface of the first layer is visible outside of the second layer.

Films formed by the present invention may be suitable for administration to at least one region of the body of the user, such as mucosal regions or regions within the body of the user, such as on the surface of internal organs. In some embodiments of the invention, the films are intended for oral administration. In other embodiments, the films are intended for topical administration. As used herein, the term "topical agent" is meant to encompass active agents that are applied to a particular surface area. For example, in one embodiment, a topical agent is applied to an area of the skin. In other embodiments, the topical agent may also be applied to mucosal areas of the body, such as the oral (e.g., buccal, sublingual, tongue), vaginal, ocular and anal areas of the body. It may be understood that films of the present invention may be capable of being applied to more than one mucosal area of the body simultaneously, such as more than one oral mucosal surface. Examples of more than one surface can include, for example, under tongue—floor of mouth, lingual—hard pallet, and buccal—gingival In still other embodiments, the topical agent is applied to an internal organ or other body surface of the user, such as during surgery, where the agent may be removed or left within the body after surgery is complete. In other embodiments, a topical agent is applied to a hard surface, such as a particular surface area in need of treatment. In other embodiments, the films of the present invention are ingestible, and are intended to be placed in the mouth of the user and swallowed as the film disintegrates and/or dissolves.

The medicament may be dispersed throughout the film, or it may be deposited onto one or more surfaces of the film. In either way, it is desirable that the amount of medicament per unit area is substantially uniform throughout the film. The "unit area" is intended to include a suitable unit area, such as the area of one typical dosage unit. It is desired that the films of the present invention where the medicament is dispersed throughout the film include a uniformity of component distribution throughout the volume of a given film. Such uniformity includes a substantially uniform amount of medicament per unit volume of the film where the unit volume is one dosage form, whether the medicament is within the matrix of the film or coated, laminated, deposited or stabilized on one or more surfaces thereof. The uniformity may include substantial uniformity of content between and among individual dosages. When such films are cut into individual units, the amount of the agent in the unit can be known with a great deal of accuracy. For the films formed herein, it is understood by one of ordinary skill in the art that the resulting film is not required to be exactly 100% uniform. All that is required is that the film be "substantially uniform", i.e., a slight amount of non-uniformity is understood to be acceptable. "Substantially uniform" may include, for example, a film that is about 90% uniform in content from one region of the film to another, or a film that is about 95% uniform in content from one region of the film to another, and most desirably about 99% uniform in content from one region of the film to another. The term "substantially uniform" may also mean that for an assay of 30 individual random samples, the relative standard deviation (RSD) shall not exceed about 7.8%, where RSD is defined as follows:

s=sample standard deviation.
$\bar{X}$=mean of the values obtained from the units tested, expressed as a percentage of the target content.
n=number of units tested.
$x_1, x_2, x_3 \ldots x_n$=individual values ($x_i$) of the units tested, expressed as a percentage of the target content.

$$s = \left[\sum\left(\frac{x_i - \bar{X}}{n-1}\right)^2\right]^{1/2}$$

$$RDS\ (\%) = \frac{100s}{\bar{X}}$$

It is desirable that any individual film products formed by the present invention (i.e., products having a substantially similar mass and volume) be substantially uniform in content with respect to each other. That is, the individual film products (including individual dosages of approximately equal sizes) formed by the present invention should have approximately the same content composition as each other film product. In some embodiments, uniformity may be determined by comparing two regions of the same film having substantially the same area, for example, taking two 1 cm$^3$ regions and comparing for uniformity. Of course, it will be understood that some deviation is to be expected during the manufacturing process, but desirably the individual film products should be at least 90% uniform in content with respect to each other. In other words, "substantially uniform" may mean that individual film products should vary by no more than about 10% with respect to each other. In some embodiments, "substantially uniform" may mean that individual film products should vary by no more than about 5% with respect to each other.

Uniformity of medicament throughout the film is important in administering an accurate and effective dose of medicament to a user. Various methods of forming uniform films, as well as various polymers, additives and fillers, may be used, including those methods and materials described in U.S. Pat. Nos. 7,425,292, 7,357,891, 7,666,337, 7,824,588 and 7,897,080, which are herein incorporated by reference in their entireties. Any number of active components or pharmaceutical agents may be included in the films discussed herein. Various combinations of active components may be used in the same film product to provide a desired effect. For example, the film may include an active and an antagonist, which may be useful for prevention of abuse of the active. The active component(s) may be disposed within any layer of film products formed herein or they may be placed onto one or more surfaces of the film products.

Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, antiviral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (commercially available as Oxycontin®); ibuprofen (commercially available as Motrin®, Advil®, Motrin Children's®, Motrin IB®), Advil Children's®, Motrin Infants'®, Motrin Junior®, Ibu-2®, Proprinal®, Ibu-200®, Midol Cramp Formula®, Bufen®, Motrin Migraine Pain®, Addaprin® and Haltran®), aspirin (commercially available as Empirin®, Ecotrin®, Genuine Bayer®, and Halfprin®), acetaminophen (commercially available as Silapap Infant's®, Silapap Children's®, Tylenol®, Tylenol Children's®, Tylenol Extra Strength®, Tylenol Infants' Original®, Tylenol Infants'®, Tylenol Arthritis®, T-Painol®, Q-Pap®, Cetafen®, Dolono®, Tycolene®, APAP®, and Aminofen®), and combinations thereof that may optionally include caffeine. Other pain relieving agents may be used in the present invention, including meperidine hydrochloride (commercially available as Demerol®), capsaicin (commercially available as Qutenza®), morphine sulfate and naltrexone hydrochloride (commercially available as Embeda®), hydromorphone hydrochloride (commercially available as Dilaudid®), propoxyphene napsylate and acetaminophen (commercially available as Darvocet-N®), Fentanyl (commercially available as Duragesic®, Onsolis®, and Fentora®), sodium hyaluronate (commercially avialble as Euflexxa®), adalimumab (commercially available as Humira®), sumatriptan succinate (commercially available as Imitrex®), fentanyl iontophoretic (commercially available as Ionsys®), orphenadrine citrate (commercially available as Norgesic®), magnesium salicylate tetrahydrate (commercially available as Novasal®), oxymorphone hydrochloride (commercially available as Opana ER®), methocarbamol (commercially available as Robaxin®), carisoprodol (commercially available as Soma®), tramadol hydrochloride (commercially available as Ultracet® and Ultram®), morphine sulfate (commercially available as MS Contin®), metaxalone (commercially available as Skelaxin®), oxycodone hydrochloride (commercially available as OxyContin®), acetaminophen/oxycodone hydrochloride (commercially available as Percocet®), oxycodone/aspirin (commercially available as Percodan®), hydrocodone bitartrate/acetaminophen (commercially available as Vicodin®), hydrocodone bitartrate/ibuprofen (commercially available as Vicoprofen®), nepafenac (commercially available as Nevanac®), and pregabalin (commercially available as Lyrica®).

The present invention may further include agents such as NSAIDs, including etodolac (commercially available as Lodine®), ketorolac tromethamine (commercially available as Acular® or Acuvail®), naproxen sodium (commercially available as Anaprox®, Naprosyn®), flurbiprofen (commercially available as Ansaid®), diclofenac sodium/misoprostol (commercially available as Arthrotec®), celecoxib (commercially available as Celebrex®), sulindac (commercially available as Clinoril®), oxaprozin (commercially available as Daypro®), piroxicam (commercially available as Feldene®), indomethacin (commercially available as Indocin®), meloxicam (commercially available as Mobic®), mefenamic acid (commercially available as Ponstel®), tolmetin sodium (commercially available as Tolectin®), choline magnesium trisalicylate (commercially available as Trilisate®), diclofenac sodium (commercially available as Voltaren®), diclofenac potassium (commercially available as Cambia® or Zipsor®), and misoprostol (commercially available as Cytotec®). Opiate agonists and antagonists, such as Buprenorphine, naloxone and nalmefene are further examples of drugs for use in the present invention.

Other preferred drugs for other preferred active ingredients for use in the present invention include anti-diarrheals such as loperamide (commercially available as Imodium ADC), Imotil®, Kaodene®, Imperim®, Diamode®, QC Anti-Diarrheal®, Health Care America Anti-Diarrheal®, Leader A-D®, and Imogen®), nitazoxanide (commercially available as Alinia®) and diphenoxylate hydrochloride/atropine sulfate (commercially available as Lomotil®), anti-histamines, anti-tussives, decongestants, vitamins, and breath fresheners. Common drugs used alone or in combination for colds, pain, fever, cough, congestion, runny nose and allergies, such as acetaminophen, ibuprofen, chlorpheniramine maleate, dextromethorphan, dextromethorphan HBr, phenylephrine HCl, pseudoephedrine HCl, diphenhydramine and combinations thereof, such as dextromethophan HBr and phenylephrine HCl (available as Triaminic®) may be included in the film compositions of the present invention.

Other active agents useful in the present invention include, but are not limited to alcohol dependence treatment, such as acamprosate calcium (commercially available as Campral®); Allergy treatment medications, such as promethazine hydrochloride (commercially available as Phenergan®), bepotastine besilate (commercially available as Bepreve®), hydrocodone polistirex/chlorpheniramine polistirex (commercially available as Tussionex®), cetirizine hydrochloride (commercially available as Zyrtec®), cetirizine hydrochloride/pseudoephedrine hydrochloride (commercially available as Zyrtec-D®), promethazine hydrochloride/codeine phosphate (commercially available as Phenergan® with Codeine), pemirolast (commercially available as Alamast®), fexofenadine hydrochloride (commercially available as Allegra®), meclizine hydrochloride (commercially available as Antivert®), azelastine hydrochloride (commercially available as Astelin®), nizatidine (commercially available as Axid®), desloratadine (commercially available as Clarinex®), cromolyn sodium (commercially available as Crolom®), epinastine hydrochloride (commercially available as Elestat®), azelastine hydrochloride (commercially available as Optivar®), prednisolone sodium phosphate (commercially available as Orapred ODT®), olopatadine hydrochloride (commercially available as Patanol®), ketotifen fumarate (commercially available as Zaditor®), and montelukast sodium (commercially available as Singulair®); and anti-histamines such as diphenhydramine HCl (available as Benadryl®), loratadine (available as Claritin®), astemizole (available as Hismanal®), nabumetone (available as Relafen®), diphenydramine HCL (available as TheraFlu®) and clemastine (available as Tavist®).

Films of the present invention may further include Alzheimer's treatment medications, such as tacrine hydrochloride (commercially available as Cognex®), galantamine (commercially available as Razadyne®), donepezil hydrochloride (commercially available as Aricept®), rivastigmine tartrate (commercially available as Exelon®), caprylidene (commercially available as Axona®), and memantine (commercially available as Namenda®); anemia medication, such as cyanocobalamin (commercially available as Nascobal®) and ferumoxytol (commercially available as Feraheme®); anesthetics, such as antipyrine with benzocaine (commercially available as Auralgan®, Aurodex® and Auroto®); angina medication, such as amlodipine besylate (commercially available as Norvasc®), nitroglycerin (commercially available as Nitro-Bid®, Nitro-Dur®, Nitrolingual®, Nitrostat®, Transderm-Nitro®), isosorbide mononitrate (commercially available as Imdur®), and isosorbide dinitrate (commercially available as Isordil®); anti-tussives such as guaifensin; anti-Alzheimer's agents, such as nicergoline; and $Ca^H$-antagonists such as nifedipine (commercially available as Procardia® and Adalat®).

Actives useful in the present invention may also include anti-asthmatics, such as albuterol sulfate (commercially available as Proventil®), ipratropium bromide (commercially available as Atrovent®), salmeterol xinafoate (commercially available as Serevent®), zafirlukast (commercially available as Accolate®), flunisolide (commercially available as AeroBid®), metaproterenol sulfate (commercially available as Alupent®), albuterol inhalation (commercially available as Ventolin®), terbutaline sulfate (commercially available as Brethine®), formoterol (commercially available as Foradil®), cromolyn sodium (commercially available as Intal®), levalbuterol hydrochloride (commercially available as Xopenex®), zileuton (commercially available as Zyflo®), fluticasone propionate/salmeterol (commercially available as Advair®), albuterol sulfate/triamcinolone acetonide (commercially available as Azmacort®), dimethylxanthine (commercially available as Theophylline®), and beclomethasone (commercially available as Beclovent®, Beconase®, Qvar®, Vancenase®, Vanceril®); angioedema medication, such as C1 esterase Inhibitor (human) (commercially available as Berinert®) and ecallantide (commercially available as Kalbitor®); and antibacterial medications, such as trimethoprim/sulfamethoxazole (commercially available as Bactrim®), mupirocin (commercially available as Bactroban®), metronidazole (commercially available as Flagyl®), sulfisoxazole acetyl (commercially available as Gantrisin®), bismuth subsalicylate and metronidazole/tetracycline hydrochloride (commercially available as Helidac Therapy®), nitrofurantoin (commercially available as Macrodantin®), norfloxacin (commercially available as Noroxin®), erythromycin ethylsuccinate/Sulfisoxazole acetyl (commercially available as Pediazole®), and levofloxacin (commercially available as Levaquin®).

The present invention may further include one or more Antibiotics, including amoxicillin (commercially available as Amoxil®), ampicillin (commercially available as Omnipen®, Polycillin® and Principen®), amoxicillin/clavulanate potassium (commercially available as Augmentin®), moxifloxacin hydrochloride (commercially available as Avelox®), besifloxacin (commercially available as Besivance®), clarithromycin (commercially available as Biaxin®), ceftibuten (commercially available as Cedax®), cefuroxime axetil (commercially available as Ceftin®), cefprozil (commercially available as Cefzil®), ciprofloxacin hydrochloride (commercially available as Ciloxan® and Cipro®), clindamycin phosphate (commercially available as Cleocin T®), doxycycline hyclate (commercially available as Doryx®), dirithromycin (commercially available as Dynabac®), erythromycin (commercially available as E.E.S.®, E-Mycin®, Eryc®, Ery-Tab®, Erythrocin®, and PCE®), erythromycin topical (commercially available as A/T/S®, Erycette®, T-Stat®), gemifloxacin (commercially available as Factive®), ofloxacin (commercially known as Ocuflox®, Floxin®), telithromycin (commercially available as Ketek®), lomefloxacin hydrochloride (commercially available as Maxaquin®), minocycline hydrochloride (commercially available as Minocin®), fosfomycin tromethamine (commercially available as Monurol®), penicillin with potassium (commercially available as Penicillin VK®, Veetids®), trimethoprim (commercially available as Primsol®), ciprofloxacin hydrochloride (commercially available as Proquin XR®), rifampin, isoniazid and pyrazinamide (commercially available as Rifater®), cefditoren (commercially available as Spectracef®), cefixime (commercially available as Suprax®), tetracycline (commercially available as Achromycin V® and Sumycin®), tobramycin (commercially available as Tobrex®), rifaximin (commercially available as Xifaxan®), azithromycin (commercially available as Zithromax®), azithromycin suspension (commercially available as Zmax®), linezolid (commercially available as Zyvox®), benzoyl peroxide and clindamycin (commercially available as BenzaClin®), erythromycin and benzoyl peroxide (commercially available as Benzamycin®), dexamethasone (commercially available as Ozurdex®), ciprofloxacin and dexamethasone (commercially available as Ciprodex®), polymyxin B sulfate/neomycin sulfate/hydrocortisone (commercially available as Cortisporin®), colistin sulfate/neomycin sulfate/hydrocortisone acetate/thonzonium bromide (commercially available as Cortisporin-TC Otic®), cephalexin hydrochloride (commercially available as Keflex®), cefdinir (commercially available as Omnicef®), and gatifloxacin (commercially available as Zymar®).

Other useful actives include cancer treatment medications, including cyclophosphamide (commercially available as Cytoxan®), methotrexate (commercially available as Rheumatrex® and Trexal®), tamoxifen citrate (commercially available as Nolvadex®), bevacizumab (commercially available as Avastin®), everolimus (commercially available as Afinitor®), pazopanib (commercially available as Votrient®), and anastrozole (commercially available as Arimidex®); leukemia treatment, such as ofatumumab (commercially available as Arzerra®); anti-thrombotic drugs, such as antithrombin recombinant lyophilized powder (commercially available as Atryn®), prasugrel (commercially available as Efient®); anti-coagulants, such as aspirin with extended-release dipyridamole (commercially available as Aggrenox®), warfarin sodium (commercially available as Coumadin®), dipyridamole (commercially available as Persantine®), dalteparin (commercially available as Fragmin®), danaparoid (commercially available as Orgaran®), enoxaparin (commercially available as Lovenox®), heparin (commercially available as Hep-Lock, Hep-Pak, Hep-Pak CVC, Heparin Lock Flush), tinzaparin (commercially available as Innohep®), and clopidogrel bisulfate (commercially available as Plavix®); antiemetics, such as granisetron hydrochloride (commercially available as Kytril®) and nabilone (commercially available as Cesamet®), trimethobenzamide hydrochloride (commercially available as Tigan®), and ondansetron hydrochloride (commercially available as Zofran®); anti-fungal treatment, such as ketoconazole (commercially available as Nizoral®), posaconazole (commercially available as Noxafil®), ciclopirox (commercially available as Penlac®), griseofulvin (commercially available as Gris-PEG®), oxiconazole nitrate (commercially available as Oxistat®), fluconazole (commercially available as Diflucan®), sertaconazole nitrate (commercially available as Ertaczo®), terbinafine hydrochloride (commercially available as Lamisil®), ciclopirox (commercially available as Loprox®), nystatin/triamcinolone acetonide (commercially available as Mycolog-II®), econazole nitrate (commercially available as Spectazole®), itraconazole (commercially available as Sporanox®), and terconazole (commercially available as Terazol®).

Active agents may further include anti-inflammatory medications, such as hydroxychloroquine sulfate (commercially available as Plaquenil®), fluticasone propionate (commercially available as Cutivate®), canakinumab (commercially available as Ilaris®), amcinonide (commercially available as Cyclocort®), methylprednisolone (commercially available as Medrol®), budesonide (commercially available as Entocort EC®), anakinra (commercially available as Kineret®), diflorasone diacetate (commercially available as Psorcon®), and etanercept (commercially available as Enbrel®); antispasmodic medication, such as phenobarbital/hyoscyamine sulfate/atropine sulfate/scopolamine hydrobromide (commercially available as Donnatal®); antiviral treatment, such as oseltamivir phosphate (commercially available as Tamiflu®); anti-parasites medication, including tinidazole (commercially available as Tindamax®); appetite treatment mediations, such as megestrol acetate (commercially available as Megace ES®), phentermine hydrochloride (commercially available as Adipex-P®), and diethylpropion hydrochloride (commercially available as Tenuate®); arthritis medications, including leflunomide (commercially available as Arava®), certolizumab pegol (commercially available as Cimzia®), diclofenac sodium (commercially available as Pennsaid®), golimumab (commercially available as Simponi®), and tocilizumab (commercially available as Actemra®); bladder control medication, such as trospium chloride (commercially available as Sanctura®), desmopressin acetate (commercially available as DDAVP®), tolterodine tartrate (commercially available as Detrol®), oxybutynin chloride (commercially available as Ditropan® or Gelnique®), darifenacin (commercially available as Enablex®), and solifenacin succinate (commercially available as VESIcare®); blood vessel constrictors, such as methylergonovine maleate (commercially available as Methergine®); plasma uric managers, such as rasburicase (commercially available as Elitek®); iron deficiency anemia medications, such as ferumoxytol (commercially available as Feraheme®); lymphoma medications, such as pralatrexate (commercially available as Folotyn®), romidepsin (commercially available as Isodax®); malaria medication, such as artemether/lumefantrine (commercially available as Coartem®); hyponatremia medication, such as tolvatpan (commercially available as Samsca®); medication for treatment of von Willebrand disease (commercially available as Wilate®); anti-hypertension medications, such as treprostinil (commercially available as Tyvaso®), tadalafil (commercially available as Adcirca®); cholesterol lowering medication, including paricalcitol (commercially available as Altocor®), pitavastatin (commercially available as Livalo®), lovastatin, niacin (commercially available as Advicor®), colestipol hydrochloride (commercially available as Colestid®), rosuvastatin calcium (commercially available as Crestor®), fluvastatin sodium (commercially available as Lescol®), atorvastatin calcium (commercially available as Lipitor®), lovastatin (commercially available as Mevacor®), niacin (commercially available as Niaspan®), pravastatin sodium (commercially available as Pravachol®), pavastatin sodium with buffered aspirin (commercially available as Pravigard PAC®), cholestyramine (commercially available as Questran®), simvastatin and niacin (commercially available as Simcor®), atenolol, chlorthalidone (commercially available as Tenoretic®), atenolol (commercially available as Tenormin®), fenofibrate (commercially available as Tricor®), fenofibrate (commercially available as Triglide®), ezetimibe/simvastatin (commercially available as Vytorin®), colesevelam (commercially available as WelChol®), bisoprolol fumarate (commercially available as Zebeta®), ezetimibe (commercially available as Zetia®), bisoprolol fumarate/hydrochlorothiazide (commercially available as Ziac®), and simvastatin (commercially available as Zocor®).

The actives included herein may also include chronic kidney disease medication, such as paricalcitol (commercially available as Zemplar®); contraceptive agents, including etonogestrel (commercially available as Implanon®), norethindrone acetate, ethinyl estradiol (commercially available as Loestrin 24 FE®), ethinyl estradiol, norelgestromin (commercially available as Ortho Evra®), levonorgestrel (commercially available as Plan B®), levonorgestrel and ethinyl estradiol (commercially available as Preven®), levonorgestrel, ethinyl estradiol (commercially available as Seasonique®), and medroxyprogesterone acetate (commercially available as Depo-Provera®); COPD medication, such as arformoterol tartrate (commercially available as Brovana®) and ipratropium bromide, albuterol sulfate (commercially available as Combivent®); cough suppressants, including benzonatate (commercially available as Tessalon®), guaifenesin, codeine phosphate (commercially available as Tussi-Organidin NR®), and acetaminophen, codeine phosphate (commercially available as Tylenol with Codeine®); medication for the treatment of diabetes, including pioglitazone hydrochloride, metformin hydrochloride (commercially available as ACTOplus Met®), bromocriptine mesylate (commercially available as Cycloset®), liraglutide (commercially available as Victoza®), saxagliptin (commercially available as Onglyza®), pioglitazone hydrochloride (commercially available as Actos®), glimepiride (commercially available as Amaryl®), rosiglitazone maleate, metformin hydrochloride (commercially available as Avandamet®), rosiglitazone maleate (commercially available as Avandaryl®), rosiglitazone maleate (commercially available as Avandia®), exenatide (commercially available as Byetta®), chlorpropamide (commercially available as Diabinese®), pioglitazone hydrochloride, glimepiride (commercially available as Duetact®), metformin hydrochloride (commercially available as Glucophage®), glipizide (commercially available as Glucotrol®), glyburide, metformin (commercially available as Glucovance®), metformin hydrochloride (commercially available as Glumetza®), sitagliptin (commercially available as Januvia®), detemir (commercially available as Levemir®), glipizide, metformin hydrochloride (commercially available as Metaglip®), glyburide (commercially available as Micronase®), repaglinide (commercially available as Prandin®), acarbose (commercially available as Precose®), nateglinide (commercially available as Starlix®), pramlintide acetate (commercially available as Symlin®), and tolazamide (commercially available as Tolinase®).

Other useful agents of the present invention may include digestive agents, such as sulfasalazine (commercially available as Azulfidine®), rabeprazole sodium (commercially available as AcipHex®), lubiprostone (commercially available as Amitiza®), dicyclomine hydrochloride (commercially available as Bentyl®), sucralfate (commercially available as Carafate®), lactulose (commercially available as Chronulac®), docusate (commercially available as Colace®), balsalazide disodium (commercially available as Colazal®), losartan potassium (commercially available as Cozaar®), olsalazine sodium (commercially available as Dipentum®), chlordiazepoxide hydrochloride, clidinium bromide (commercially available as Librax®), esomeprazole magnesium (commercially available as Nexium®), famotidine (commercially available as Pepcid®), lansoprazole (commercially available as Prevacid®), lansoprazole and naproxen (commercially available as Prevacid NapraPAC®), amoxicillin/clarithromycin/lansoprazole (commercially available as Prevpac®), omeprazole (commercially available as Prilosec®), pantoprazole sodium (commercially available as Protonix®), metoclopramide hydrochloride (commercially available as Reglan® or Metozolv®), cimetidine (commercially available as Tagamet®), ranitidine hydrochloride (commercially available as Zantac®), and omeprazole, sodium bicarbonate (commercially available as Zegerid®); diuretics, including spironolactone, hydrochlorothiazide (commercially available as Aldactazide®), spironolactone (commercially available as Aldactone®). bumetanide (commercially available as Bumex®), torsemide (commercially available as Demadex®), chlorothiazide (commercially available as Diuril®), furosemide (commercially available as Lasix®), metolazone (commercially available as Zaroxolyn®), and hydrochlorothiazide, triamterene (commercially available as Dyazide®).

Agents useful herein may also include treatment for emphysema, such as tiotropium bromide (commercially available as Spiriva®); fibromyalgia medication, such as milnacipran hydrochloride (commercially available as Savella®); medication for the treatment of gout, such as colchicine (commercially available as Colcrys®), and febuxostat (commercially available as Uloric®); enema treatments, including aminosalicylic acid (commercially available as Mesalamine® and Rowasa®); epilepsy medications, including valproic acid (commercially available as Depakene®), felbamate (commercially available as Felbatol®), lamotrigine (commercially available as Lamictal®), primidone (commercially available as Mysoline®), oxcarbazepine (commercially available as Trileptal®), zonisamide (commercially available as Zonegran®), levetiracetam (commercially available as Keppra®), and phenytoin sodium (commercially available as Dilantin®).

Erectile dysfunction therapies useful herein include, but are not limited to, drugs for facilitating blood flow to the penis, and for effecting autonomic nervous activities, such as increasing parasympathetic (cholinergic) and decreasing sympathetic (adrenersic) activities. Useful agents for treatment of erectile dysfunction include, for example, those agents available as alprostadil (commercially available as Caverject®), tadalafil (commercially available as Cialis®), vardenafil (commercially available as Levitra®), apomorphine (commercially available as Uprima®), yohimbine hydrochloride (commercially available as Aphrodyne®, Yocon®), and sildenafil citrate (commercially available as Viagra®).

Agents useful herein may further include eye medications and treatment, such as dipivefrin hydrochloride (commercially available as Propine®), valganciclovir (commercially available as Valcyte®), ganciclovir ophthalmic gel (commercially available as Zirgan®); bepotastine besilate (commercially available as Bepreve®), besifloxacin (commercially available as Besivance®), bromfenac (commercially available as Xibrom®), fluorometholone (commercially available as FML®), pilocarpine hydrochloride (commercially available as Pilocar®), cyclosporine (commercially available as Restasis®), brimonidine tartrate (commercially available as Alphagan P®), dorzolamide hydrochloride/timolol maleate (commercially available as Cosopt®), bimatoprost (commercially available as Lumigan®), timolol maleate (available as Timoptic®), travoprost (commercially available as Travatan®), latanoprost (commercially available as Xalatan®), echothiophate iodide (commercially available as Phospholine Iodide®), and ranibizumab (commercially available as Lucentis®); fluid controllers, such as acetazolamide (commercially available as Diamox®); gallstone medications, including ursodiol (commercially available as Actigall®); medication for the treatment of gingivitis, including chlorhexidine gluconate (commercially available as Peridex®); headache medications, including butalbital/codeine phosphate/aspirin/caffeine (commercially available as Fiornal® with Codeine), naratriptan hydrochloride (commercially available as Amerge®), almotriptan (commercially available as Axert®), ergotamine tartrate/caffeine (commercially available as Cafergot®), butalbital/acetaminophen/caffeine (commercially available as Fioricet®), butalbital/aspirin/caffeine (commercially available as Fiorinal®), frovatriptan succinate (commercially available as Frova®), rizatriptan benzoate (commercially available as Maxalt®), isometheptene mucate/dichloralphenazone/acetaminophen (commercially available as Midrin®), dihydroergotamine mesylate (commercially available as Migranal®), eletriptan hydrobromide (commercially available as Relpax®), and zolmitriptan (commercially available as Zomig®); influenza medication, such as haemophilus b conjugate vaccine; tetanus toxoid conjugate (commercially available as Hiberix®); and heart treatments, including quinidine sulfate, isosorbide dinitrate/hydralazine hydrochloride (commercially available as BiDil®), digoxin (commercially available as Lanoxin®), flecainide acetate (commercially available as Tambocor®), mexiletine hydrochloride (commercially available as Mexitil®), disopyramide phosphate (commercially available as Norpace®), procainamide hydrochloride (commercially available as Procanbid®), and propafenone (commercially available as Rythmol®).

Other useful agents include hepatitis treatments, including entecavir (commercially available as Baraclude®), hepatitis B immune globulin (commercially available as HepaGam B®), and copegus/rebetol/ribasphere/vilona/virazole (commercially available as Ribavirin®); herpes treatments, including valacyclovir hydrochloride (commercially available as Valtrex®), penciclovir (commercially available as Denavir®), acyclovir (commercially available as Zovirax®), and famciclovir (commercially available as Famvir®); treatment for high blood pressure, including enalaprilat (available as Vasotec®), captopril (available as Capoten®) and lisinopril (available as Zestril®), verapamil hydrochloride (available as Calan®), ramipril (commercially available as Altace®), olmesartan medoxomil (commercially available as Benicar®), amlodipine/atorvastatin (commercially available as Caduet®), nicardipine hydrochloride (commercially available as Cardene®), diltiazem hydrochloride (commercially available as Cardizem®), quinapril hydrochloride (commercially available as Accupril®), quinapril hydrochloride/hydrochlorothiazide (commercially available as Accuretic®), perindopril erbumine (commercially available as Aceon®), candesartan cilexetil (commercially available as Atacand®), candesartan cilexetil/hydrochlorothiazide (commercially available as Atacand HCT®), irbesartan/hydrochlorothiazide (commercially available as Avalide®), irbesartan (commercially available as Avapro®), amlodipine besylate/olmesartan medoxomil (commercially available as Azor®), levobunolol hydrochloride (commercially available as Betagan®), betaxolol hydrochloride (commercially available as Betoptic®), nebivolol (commercially available as Bystolic®), captopril/hydrochlorothiazide (commercially available as Capozide®), doxazosin mesylate (commercially available as Cardura®), clonidine hydrochloride (commercially available as Catapres®), carvedilol (commercially available as Coreg®), nadolol (commercially available as Corgard®), nadolol/bendroflumethiazide (commercially available as Corzide®), valsartan (commercially available as Diovan®), isradipine (commercially available as DynaCirc®), Guanabenz acetate. (commercially available as Wytensin®), Guanfacine hydrochloride (commercially available as Tenex® or Intuniv®), losartan potassium/hydrochlorothiazide (commercially available as Hyzaar®), propranolol hydrochloride (commercially available as Indera®), propranolol hydrochloride/hydrochlorothiazide (commercially available as Inderide®), eplerenone (commercially available as Inspra®), ambrisentan (commercially available as Letairis®), enalapril maleate/felodipine (commercially available as Lexxel®), metoprolol tartrate (commercially available as Lopressor®), benazepril hydrochloride (commercially available as Lotensin®), benazepril hydrochloride/hydrochlorothiazide (commercially available as Lotensin HCT®), amlodipine/benazepril hydrochloride (commercially available as Lotrel®), indapamide (commercially available as Lozol®), trandolapril (commercially available as Mavik®), telmisartan (commercially available as Micardis®), telmisartan/hydrochlorothiazide (commercially available as Micardis HCT®), prazosin hydrochloride (commercially available as Minipress®), amiloride, hydrochlorothiazide (commercially available as Moduretic®), fosinopril sodium (commercially available as ZZXT Monopril®), fosinopril sodium/hydrochlorothiazide (commercially available as Monopril-HCT®), pindolol (commercially available as Visken®), felodipine (commercially available as Plendil®), sildenafil citrate (commercially available as Revatio®), Nisoldipine (commercially available as Sular®), trandolapril/verapamil hydrochloride (commercially available as Tarka®), aliskiren (commercially available as Tekturna®), eprosartan mesylate (commercially available as Teveten®), eprosartan mesylate/hydrochlorothiazide (commercially available as Teveten HCT®), moexipril hydrochloride/hydrochlorothiazide (commercially available as Uniretic®), moexipril hydrochloride (commercially available as Univasc®), enalapril maleate/hydrochlorothiazide (commercially available as Vaseretic®), and lisinopril/hydrochlorothiazide (commercially available as Zestoretic®).

The present invention may include agents useful in the medication for the treatment of HIV/AIDS, such as amprenavir (commercially available as Agenerase®), tipranavir (commercially available as Aptivus®), efavirenz/emtricitabine/tenofovir (commercially available as Atripla®), lamivudine/zidovudine (commercially available as Combivir®), indinavir sulfate (commercially available as Crixivan®), lamivudine (commercially available as Epivir®), saquinavir (commercially available as Fortovase®), zalcitabine (commercially available as Hivid®), lopinavir/ritonavir (commercially available as Kaletra®), fosamprenavir calcium (commercially available as Lexiva®), ritonavir (commercially available as Norvir®), zidovudine (commercially available as Retrovir®), atazanavir sulfate (commercially available as Reyataz®), efavirenz (commercially available as Sustiva®), abacavir/lamivudine/zidovudine (commercially available as Trizivir®), didanosine (commercially available as Videx®), nelfinavir mesylate (commercially available as Viracept®), nevirapine (commercially available as Viramune®), tenofovir disoproxil fumarate (commercially available as Viread®), stavudine (commercially available as Zerit®), and abacavir sulfate (commercially available as Ziagen®); homocysteiene removers, including betaine anhydrous (commercially available as Cystadane®); medications, such as insulin (commercially available as Apidra®, Humalog®, Humulin®, Iletin®, and Novolin®); and HPV treatment, such as Human papillomavirus vaccine (commercially available as Gardasil®) or human papillomavirus bivalent (commercially available as Cervarix®); immunosuppressants, including cyclosporine (commercially available as Gengraf®, Neoral®, Sandimmune®, and Apo-Cyclosporine®).

Agents useful in the present invention may further include prolactin inhibitors, such as bromocriptine mesylate (commercially available as Parlodel®); medications for aiding in stress tests, such as regadenoson (commercially available as Lexiscan®); baldness medication, including finasteride (commercially available as Propecia® and Proscar®); pancreatitis treatment, such as gemfibrozil (commercially available as Lopid®); hormone medications, such as norethindrone acetate/ethinyl estradiol (commercially available as femHRT®), goserelin acetate (commercially available as Zoladex®), progesterone gel (commercially available as Prochieve®), progesterone (commercially available as Prometrium®), calcitonin-salmon (commercially available as Miacalcin®), calcitriol (commercially available as Rocaltrol®), Synthroid (commercially available as Levothroid®, Levoxyl®, Unithroid®), testosterone (commercially available as Testopel®, Androderm®, Testoderm®, and AndroGel®); menopause medication, such as estradiol/norethindrone acetate (commercially available as Activella®), drospirenone/estradiol (commercially available as Angeliq®), estradiol/levonorgestrel (commercially available as Climara Pro®), estradiol/norethindrone acetate (commercially available as CombiPatch®), estradiol (commercially available as Estrasorb®, Vagifem® and Estro-Gel®), esterified estrogens and methyltestosterone (commercially available as Estratest®), estrogen (commercially available as Alora®, Climara®, Esclim®, Estraderm®, Vivelle®, Vivelle-Dot®), estropipate (commercially available as Ogen®), conjugated estrogens (commercially available as Premarin®), and medroxyprogesterone acetate (commercially available as Provera®); menstrual medications, including leuprolide acetate (commercially available as Lupron Depot), tranexamic acid (commercially available as Lysteda®), and norethindrone acetate (commercially available as Aygestin®); and muscle relaxants, including cyclobenzaprine hydrochloride (commercially available as Flexeril®), tizanidine (commercially available as Zanaflex®), and hyoscyamine sulfate (commercially available as Levsin®).

Agents useful herein may also include osteoporosis medications, including ibrandronate sodium (commercially available as Boniva®), risedronate (commercially available as Actonel®), raloxifene hydrochloride (commercially available as Evista®, Fortical®), and alendronate sodium (commercially available as Fosamax®); ovulation enhancers, including clomiphene citrate (commercially available as Serophene®, Clomid®, Serophene®); Paget's disease treatment, such as etidronate disodium (commercially available as Didronel®); pancreatic enzyme deficiency medications, such as pancrelipase (commercially available as Pancrease® or Zenpep®); medication for the treatment of Parkinson's disease, such as pramipexole dihydrochloride (commercially available as Mirapex®), ropinirole hydrochloride (commercially available as Requip®), carbidopa/levodopa (commercially available as Sinemet CRC), carbidopa/levodopa/entacapone (commercially available as Stalevo®), selegiline hydrochloride (commercially available as Zelapar®), rasagiline (commercially available as Azilect®), entacapone (commercially available as Comtan®), and selegiline hydrochloride (commercially available as Eldepryl®); multiple sclerosis medication, such as dalfampridine (commercially available as Ampyra®) and interferon beta-I b (commercially available as Extavia®); prostate medication, including flutamide (commercially available as Eulexin®), nilutamide (commercially available as Nilandron®), dutasteride (commercially available as Avodart®), tamsulosin hydrochloride (commercially available as Flomax®), terazosin hydrochloride (commercially available as Hytrin®), and alfuzosin hydrochloride (commercially available as UroXatral®).

Films of the present invention may further include psychiatric medications, including alprazolam (available as Niravam®, Xanax®), clozopin (available as Clozaril®), haloperidol (available as Haldol®), fluoxetine hydrochloride (available as Prozac®), sertraline hydrochloride (available as Zoloft®), asenapine (commercially available as Saphris®), iloperidone (commercially available as Fanapt®), paroxtine hydrochloride (available as Paxil®), aripiprazole (commercially aavialbe as Abilify®), guanfacine (commercially available as Intuniv®), Amphetamines and methamphetamines (commercially available as Adderall® and Desoxyn®), clomipramine hydrochloride (commercially available as Anafranil®), Buspirone hydrochloride (commercially available as BuSpar®), citalopram hydrobromide (commercially available as Celexa®), duloxetine hydrochloride (commercially available as Cymbalta®), methylphenidate (commercially available as Ritalin, Daytrana®), divalproex sodium (Valproic acid) (commercially available as Depakote®), dextroamphetamine sulfate (commercially available as Dexedrine®), venlafaxine hydrochloride (commercially available as Effexor®), selegiline (commercially available as Emsam®), carbamazepine (commercially available as Equetro®), lithium carbonate (commercially available as Eskalith®), fluvoxamine maleate/dexmethylphenidate hydrochloride (commercially available as Focalin®), ziprasidone hydrochloride (commercially available as Geodon®), ergoloid mesylates (commercially available as Hydergine®), escitalopram oxalate (commercially available as Lexapro®), chlordiazepoxide (commercially available as Librium®), molindone hydrochloride (commercially available as Moban®), phenelzine sulfate (commercially available as Nardil®), thiothixene (commercially available as Navane®), desipramine hydrochloride (commercially available as Norpramin®), benzodiazepines (such as those available as Oxazepam®), nortriptyline hydrochloride (commercially available as Pamelor®), tranylcypromine sulfate (commercially available as Parnate®), prochlorperazine, mirtazapine (commercially available as Remeron®), risperidone (commercially available as Risperdal®), quetiapine fumarate (commercially available as Seroquel®), doxepin hydrochloride (commercially available as Sinequan®), atomoxetine hydrochloride (commercially available as Strattera®), trimipramine maleate (commercially available as Surmontil®), olanzapine/fluoxetine hydrochloride (commercially available as Symbyax®), imipramine hydrochloride (commercially available as Tofranil®), protriptyline hydrochloride (commercially available as Vivactil®), bupropion hydrochloride (commercially available as Wellbutrin®, Wellbutrin SR®, and Wellbutrin XR®), and olanzapine (commercially available as Zyprexa®).

Agents useful herein may also include uric acid reduction treatment, including allopurinol (commercially available as Zyloprim®); seizure medications, including gabapentin (commercially available as Neurontin®), ethotoin (commercially available as Peganone®), vigabatrin (commercially available as Sabril®), and topiramate (commercially available as Topamax®); treatment for shingles, such as zoster vaccine live (commercially available as Zostavax®); skin care medications, including calcipotriene (commercially available as Dovonex®), ustekinumab (commercially available as Stelara®), televancin (commercially available as Vibativ®), isotretinoin (commercially available as Accutane®), hydrocortisone/iodoquinol (commercially available as Alcortin®), sulfacetamide sodium/sulfur (commercially available as Avar®), azelaic acid (commercially available as Azelex®, Finacea®), benzoyl peroxide (commercially available as Desquam-E®), adapalene (commercially available as Differin®), fluorouracil (commercially available as Efudex®), pimecrolimus (commercially available as Elidel®), topical erythromycin (commercially available as A/T/S®, Erycette®, T-Stat®), hydrocortisone (commercially available as Cetacort®, Hytone®, Nutracort®), metronidazole (commercially available as MetroGel®), doxycycline (commercially available as Oracea®), tretinoin (commercially available as Retin-A® and Renova®), mequinol/tretinoin (commercially available as Solage®), acitretin (commercially available as Soriatane®), calcipotriene hydrate/betamethasone dipropionate (commercially available as Taclonex®), tazarotene (commercially available as Tazorac®), fluocinonide (commercially available as Vanos®), desonide (commercially available as Verdeso®), miconazole nitrate/Zinc oxide (commercially available as Vusion®), ketoconazole (commercially available as Xolegel®), and efalizumab (commercially available as Raptiva®).

Other agents useful herein may include Sleep disorder medications, including zaleplon (available as Sonata®), eszopiclone (available as Lunesta®), zolpidem tartrate (commercially available as Ambient, Ambien CR®, Edluar®), lorazepam (commercially available as Ativan®), flurazepam hydrochloride (commercially available as Dalmane®), triazolam (commercially available as Halcion®), clonazepam (commercially available as Klonopin®), barbituates, such as Phenobarbital®), Modafinil (commercially available as Provigil®), temazepam (commercially available as Restoril®), ramelteon (commercially available as Rozerem®), clorazepate dipotassium (commercially available as Tranxene®), diazepam (commercially available as Valium®), quazepam (commercially available as Doral®), and estazolam (commercially available as ProSom®); smoking cessation medications, such as varenicline (commercially available as Chantix®), nicotine, such as Nicotrol®, and bupropion hydrochloride (commercially available as Zyban®); and steroids, including alclometasone dipropionate (commercially available as Aclovate®), betamethasone dipropionate (commercially available as Diprolene®), mometasone furoate (commercially available as Elocon®), fluticasone (commercially available as Flonase®, Flovent®, Flovent Diskus®, Flovent Rotadisk®), fluocinonide (commercially available as Lidex®), mometasone furoate monohydrate (commercially available as Nasonex®), desoximetasone (commercially available as Topicort®), clotrimazole/betamethasone dipropionate (commercially available as Lotrisone®), prednisolone acetate (commercially available as Pred Forte®, Prednisone®, Budesonide Pulmicort®, Rhinocort Aqua®), prednisolone sodium phosphate (commercially available as Pediapred®), desonide (commercially available as Tridesilon®), and halobetasol propionate (commercially available as Ultravate®).

Films of the present invention may further include agents useful for thyroid disease treatment, such as hormones TC and TD (commercially available as Armour Thyroid®); potassium deficiency treatment, including potassium chloride (commercially available as Micro-K®); triglycerides regulators, including omega-3-acid ethyl esters (commercially available as Omacor®); urinary medication, such as phenazopyridine hydrochloride (commercially available as Pyridium®) and methenamine, methylene blue/phenyl salicylate/benzoic acid/atropine sulfate/hyoscyamine (commercially available as Urised®); prenatal vitamins (commercially available as Advanced Natalcare®, Materna®, Natalins®, Prenate Advance®); weight control medication, including orlistat (commercially available as Xenical®) and sibutramine hydrochloride (commercially available as Meridia®).

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

The pharmaceutically active agents employed in the present invention may be in amorphous or crystalline form, incorporated into nanoparticles or combinations thereof.

The process may include depositing a wet film matrix onto the surface of a substrate. Any desired substrate may be used, including, for example, mylar, paper, plastic, metal, foil, and combinations thereof. The substrate may be laminated if desired. Further, the substrate may be chemically treated on one or more surfaces prior to depositing the wet film matrix thereon. Desirably, the substrate is substantially flat, but is flexible to allow for rolling, such as for storage or for packaging of the formed film products. The substrate may include one or more dams, such as that disclosed in Applicant's co-pending U.S. patent application Ser. No. 12/711,883, filed Feb. 24, 2010, the entire contents of which are incorporated by reference herein.

In some embodiments, the substrate 20 may include a pre-formed sheet of dissolvable and/or ingestible film, where the wet film-forming matrix is deposited onto the sheet, providing a multi-layered film product. In still other embodiments, the substrate may include a plurality of pre-formed film products on its surface, and the wet film matrix is deposited onto the surface of the pre-formed film products.

Products of the present invention may be made through any desired processing means, including methods described above. In some embodiments, products of the present invention may be made through a multiple lane processing method and apparatus. Such methods may allow for adjustments and modifications to be made to the products as they are being formed, thus reducing the amount of wasted materials and, in particular, wasted active components. As explained above, typical processing methods require adjustment of the film-forming material during processing. Film that is formed prior to such adjustment is typically not suitable for use, and must be discarded. The multiple lane method described herein allows for adjustments to be made while avoiding or reducing the amount of wasted active.

Generally, film products are formed through applying at least one layer of a wet film forming matrix onto a substrate and allowing the at least one layer of the wet film forming matrix to dry to form a resulting film. Applying the layer of film may include, for example, coating, casting, extruding, cast film extrusion or other methods of applying the wet film forming material. The current minimum batch size that is typically applied onto production equipment today is about 4 kg. Although attempts are made to form a resulting film having all desired physical properties, typical processing takes at least one or more than one attempts to achieve a resulting product having all desired physical properties. To be suitable for use, a resulting film product should meet certain pre-determined standards, i.e., a particular weight, thickness, content uniformity, moisture content, and the like. After a film product is formed, it is tested for conformity with any one or more of the pre-determine standards and, if the product does not meet any desired standard, the procedure is modified, a new product is formed, and the original product is discarded.

When a new batch is initially being formed, that is, when the layer of wet film forming matrix is first placed into the apparatus (i.e., onto a substrate) and the drying process begins, the film product that is produced in the initial stages typically has incorrect final properties. That is, the resulting film from the initial stages of formation may have a weight that is too large or small, a thickness that is too big or small, a moisture content that is too high or low, a non-uniform drug distribution throughout the film, a drug content that may be inaccurate, or any number of properties that make the resulting product unacceptable for use. In addition, the resulting product should be free of visible defects, such as cracking or hazing. If the resulting film suffers from a defect of any of these properties, the processing parameters of the film forming assembly may be adjusted to correct for these properties.

The adjustment of processing parameters typically requires that the film forming material travel through the entire drying apparatus, such as an oven, after the change before a sample of the resulting film may be taken and measured to ensure that the desired properties have been reached. This is important because, after the adjustment is made, the process must be repeated in full to achieve the resulting film that can be tested. For one particular drying apparatus, the adjustment period may take more than 20 meters of film per adjustment. Thus, the resulting product will include at least 20 meters of wasted material, which is not suitable for use and must be discarded. In some instances, the adjustment that was made may not result in a proper product, and further adjustments must be made, which results in even more wasted material.

Serious problems and expenses arise when the wasted material includes expensive materials, such as actives and other similar materials. During the initial film forming period, during the adjustment period and any subsequent adjustment period, the resulting film is wasted and must be scrapped. If this material includes actives, the amount of wasted material may result in an incredibly high expense.

For limited supply materials or for expensive drugs, steps have previously been taken to produce as small a batch as possible to prepare a suitable film. Until now, these small batches have been prepared in a laboratory setting using batches as small as 200 grams. At a typical coat weight of about 10 mg/cm$^2$, coating 25 mm wide, at 30% active loading, the resulting product will be about 24 meters of film. Even this reduced amount of material constitutes unnecessary wasted material and, for costly actives, may be very expense.

Thus, the multiple lane processing method and apparatus described herein seeks to avoid the expense of wasted active-containing film and thus may significantly reduce the processing expense associated with the formation of such films. Essentially, the method includes applying very small batches of the film-forming material on full sized production equipment by using a surrogate solution in parallel with an active solution so as to set up proper processing parameters.

A multiple lane film forming apparatus for forming an active-containing film product may be included in this invention. Such apparatuses and methods of using these apparatuses may include those depicted in the Figures. Of course, the Figures herein represent examples of apparatuses useful herein but modifications may be made as desired. FIGS. 1A-1D depict representative apparatuses using individual pumps to feed lanes of material onto a substrate. FIGS. 2A-2D are similar apparatuses, but use slot die coating methods.

With reference to FIGS. 1A-1D, a typical apparatus 10 includes a substrate 20, which may be a movable substrate 20 including a first lane 30 and a second lane 40 substantially parallel to the first lane 30. If desired, indicia may be provided on the substrate to show the position of the lanes, or alternatively, no indicia may be provided. The lanes 30, 40 are formed by deposition of the film forming material onto the substrate, as will be described below. The lanes of film forming material 30, 40 may be formed through the use of a coating head that is capable of depositing film forming material into the desired lane. For example, the coating head may include 2 sets of parallel side dams (50A-50D), between which the film forming material is deposited to form the desired lane. For example, dams 50A and 50B deposit material to form lane 30 therebetween. Similarly, dams 50C and 50D deposit material to form lane 40 therebetween. The dams 50A-50D form the coating reservoirs for the coating roller 60. Although only two lanes (30, 40) are depicted in FIGS. 1A-1B and 2A-2B, and three lanes (30, 40, 40') are depicted in FIGS. 1C-1D and 2C-2D, it is to be understood that any number of lanes may be used as desired, depending upon the width of each lane and the overall width of the substrate 20. It is further understood that the widths of the individual lanes may vary. Typically, the lanes (30, 40) will have substantially the same width and therefore provide substantially the same size end product. However, the active-containing lane may be wider or narrower than the surrogate lane, if desired. For example, lane 30 may have a width that is 20% to 500% the size of lane 40, or it may be 33% to 300% the size of lane 40. Lane 30 may have a width that is between 50% and 200% the width of lane 40, and more desirably a width that is between 90 to 110% the width of lane 40. In general, the closer the two lanes (30, 40) are in width, the closer the coating parameters will be to the optimum for the active film.

The apparatus 10 further includes a drying apparatus 70 sized to accommodate the substrate and having a length suitable for achieving the desired drying of a film product. The apparatus 10 should additionally include at least a first feeding reservoir 80A and first feed line 90A to feed a first batch of film forming material 100A to the first lane 30 and a second feeding reservoir 80B and second feed line 90B to feed a second batch of film forming material 100B to the second lane 40. The first and second feed lines 90A, 90B each lead to a separate pump (110A, 110B), which dispenses the desired amount of film forming material to the lanes (30, 40).

Figure 2A:
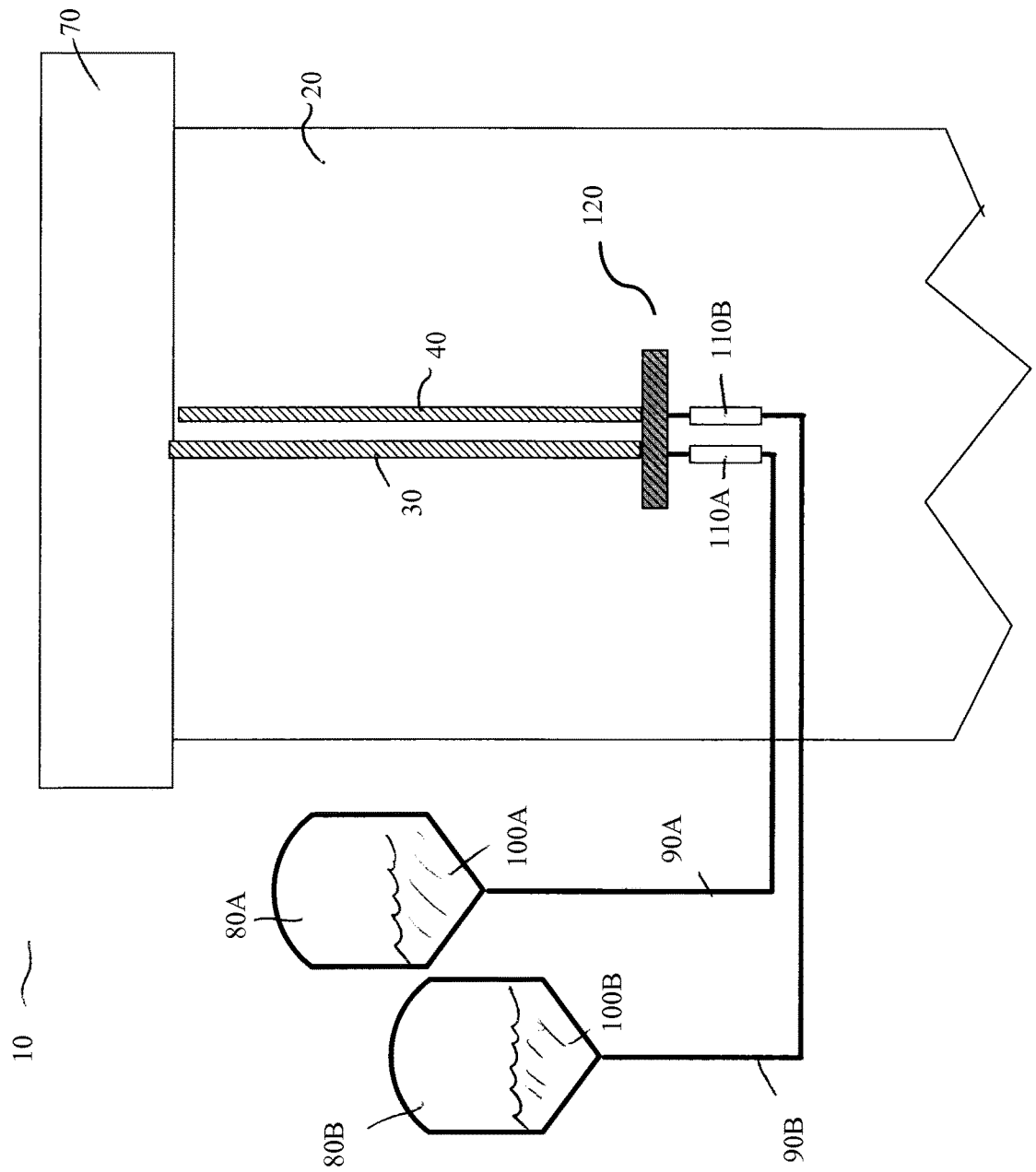
FIGS. 2A-2B depict an apparatus useful in the present invention, where two lanes of film are formed using a slot die application.
Figure 2B:
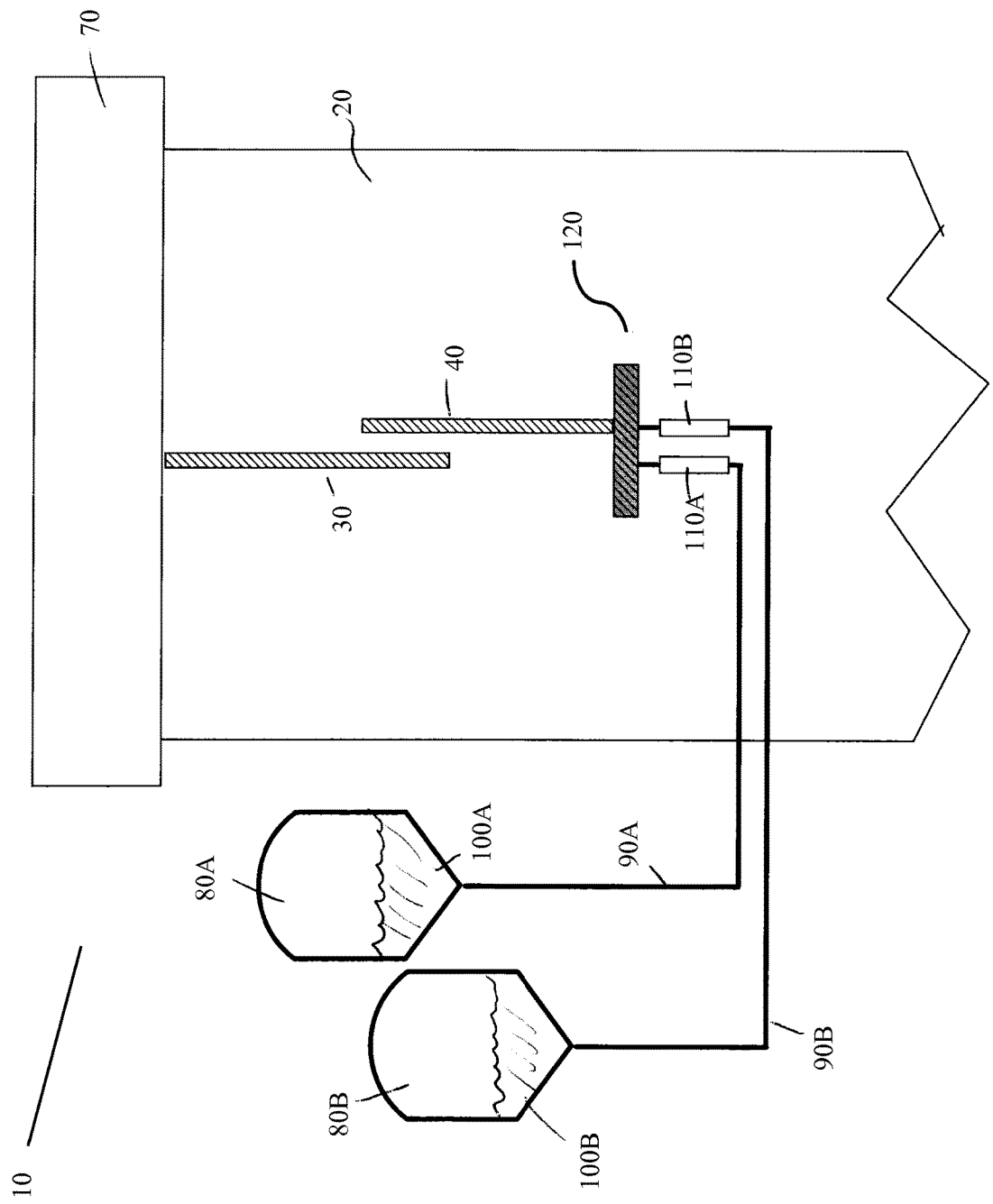
Figure 2C:
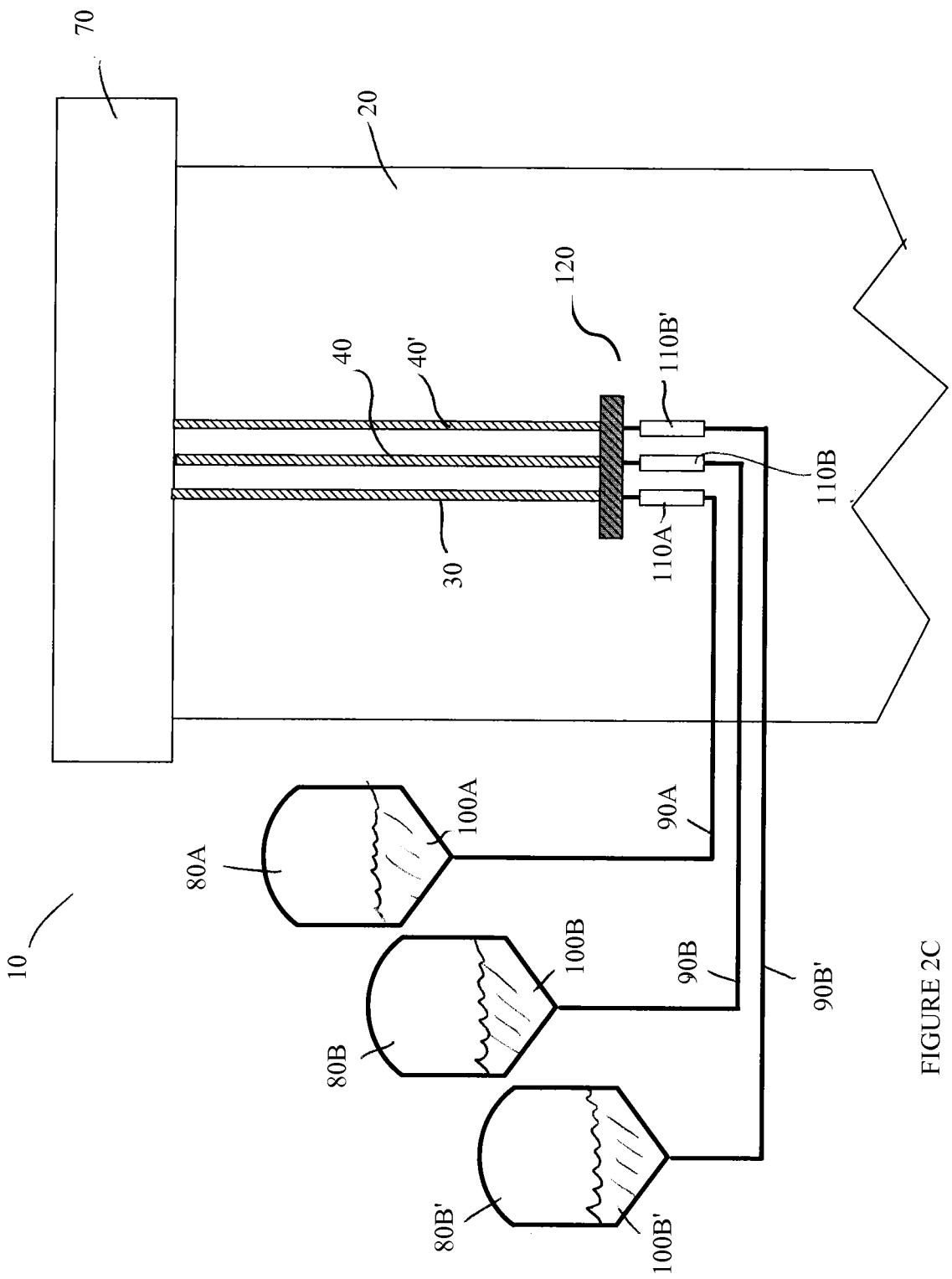
FIGS. 2C-2D depicts another apparatus useful in the present invention, where more than two lanes of film are formed using a slot die coating application.
Figure 2D:
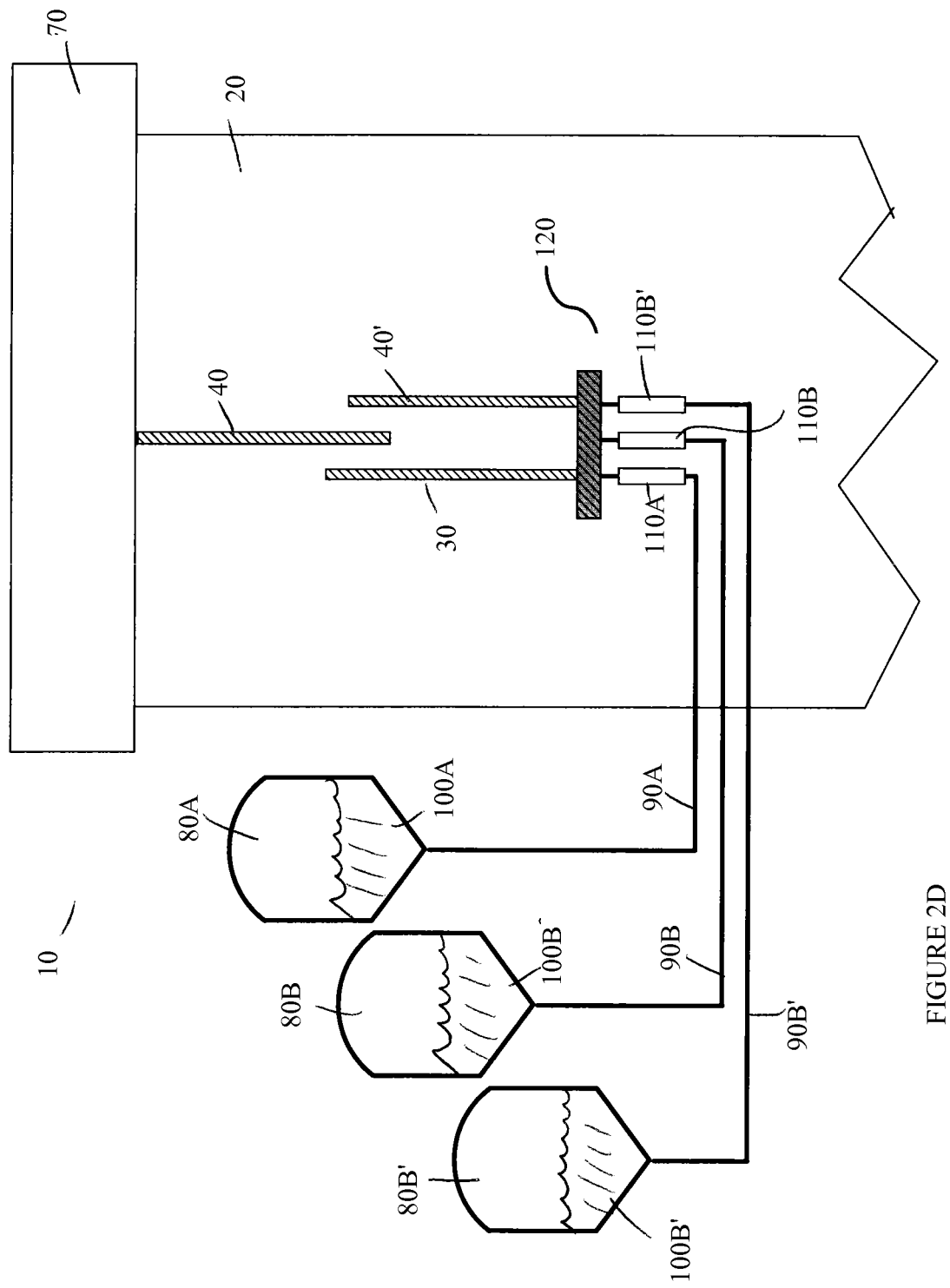

If desired, the apparatus 10 may include one coating roller 60, which is sized and suitable for coating one or more than one batches to any number of lanes in the apparatus 10. As depicted, it is particularly desirable to include a plurality of separate batch reservoirs 80A, 80B, each of which is designed to contain a particular film forming batch 100A, 100B, and is capable of being fed to the coating roller(s) 60. If desired, as depicted in FIGS. 2A-2D, the apparatus 10 may include a slot die coating system for dispensing the film forming material. In such slot die systems, the pumps 110A, 110B may feed material into a slot die coating head 120, which dispenses the film forming material into any desired number of lanes (e.g., 30, 40) through a plurality of orifices (not seen in Figures). Slot die coating systems may be particularly useful for preparing very small film strips. As explained above, any number of lanes of film material may be formed as desired, with FIGS. 2A-2B showing two lanes (30, 40) and FIGS. 2C-2D showing three lanes (30, 40, 40').

The apparatus 10, whether it includes a coating head system or a slot die system, may be useful in the multiple lane processing method described below. It is understood that the below method describes one particular embodiment of using the apparatus, but various modifications to the processing steps may be made without changing the scope and spirit of the invention.

In one desirable embodiment of the multiple lane processing method, the procedure includes two separate processing stages. A first stage is the surrogate film forming stage. As will be described in detail below, this first stage for the formation of a surrogate film product includes film-forming components and less active component than the second stage film, so as to avoid wasting of precious materials such as actives. In some embodiments, the surrogate film may include no active. The end result of the first stage is the formation of a surrogate film product, which includes minimal, if any, active. After the first stage is complete, the process undergoes a "lane switch", in which the apparatus begins forming a second film product, most desirably in a second lane (or in multiple lanes, if desired). The second stage is the active containing film forming stage. As will be described in detail below, this second stage includes formation of a film product including film-forming materials and any desired active components. Since the processing parameters for the film development have been set during the surrogate film forming stage, there will be little to no wasted materials during the second stage; in particular, there will be little to no wasted active components during the second stage. Other intermediate stages may be present in the process if desired.

In one particular embodiment, at least a first lane 30 is used in the apparatus 10. The first lane 30 includes a deposited lane of film forming material, which may be formed in a separate substrate 20, such as a mylar or paper substrate. In other embodiments, the lane 30 may be formed in a separate dissolvable or disintegrable film product, so as to form a multi-layered film product. For example, the substrate 20 may include a layer of film material, upon which the lane 30 of film forming material is deposited (such as via casting, extrusion, and the like). The first lane 30 may be formed through the use of a parallel set of dams 50A, 50B, creating a lane between the dams. The apparatus 10 may include a second lane 40 of film forming material, and optionally three or more lanes. These additional lanes may be formed through the use of dams as described above. Thus, for a two-lane embodiment, there may be four sets of parallel dams. For a three-lane embodiment, there may be six sets of parallel dams. In alternate embodiments, each lane may simply be extruded onto the surface of a substrate 20 in such a fashion that side walls or dams are unnecessary. This may typically be achieved when the viscosity of the film forming material is sufficiently high and substantially maintains its shape and thickness after being applied to the substrate.

For ease of reference, the procedure described herein will refer to two lanes, although it is understood that any number of lanes may be used in the process.

Figure 1C:
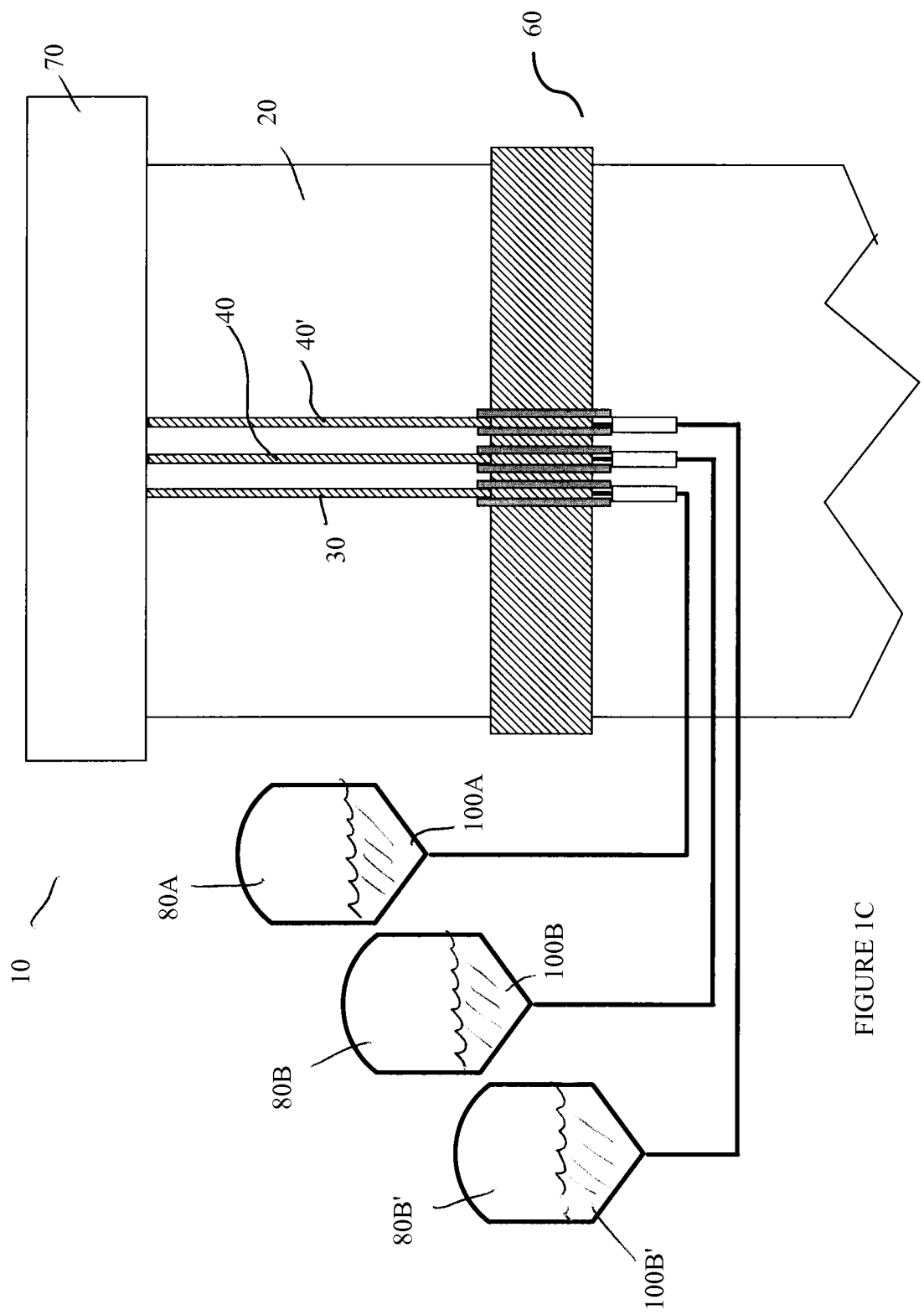
FIGS. 1C-1D depicts another apparatus useful in the present invention, where more than two lanes of film are formed using a coating roller system.
Figure 1D:
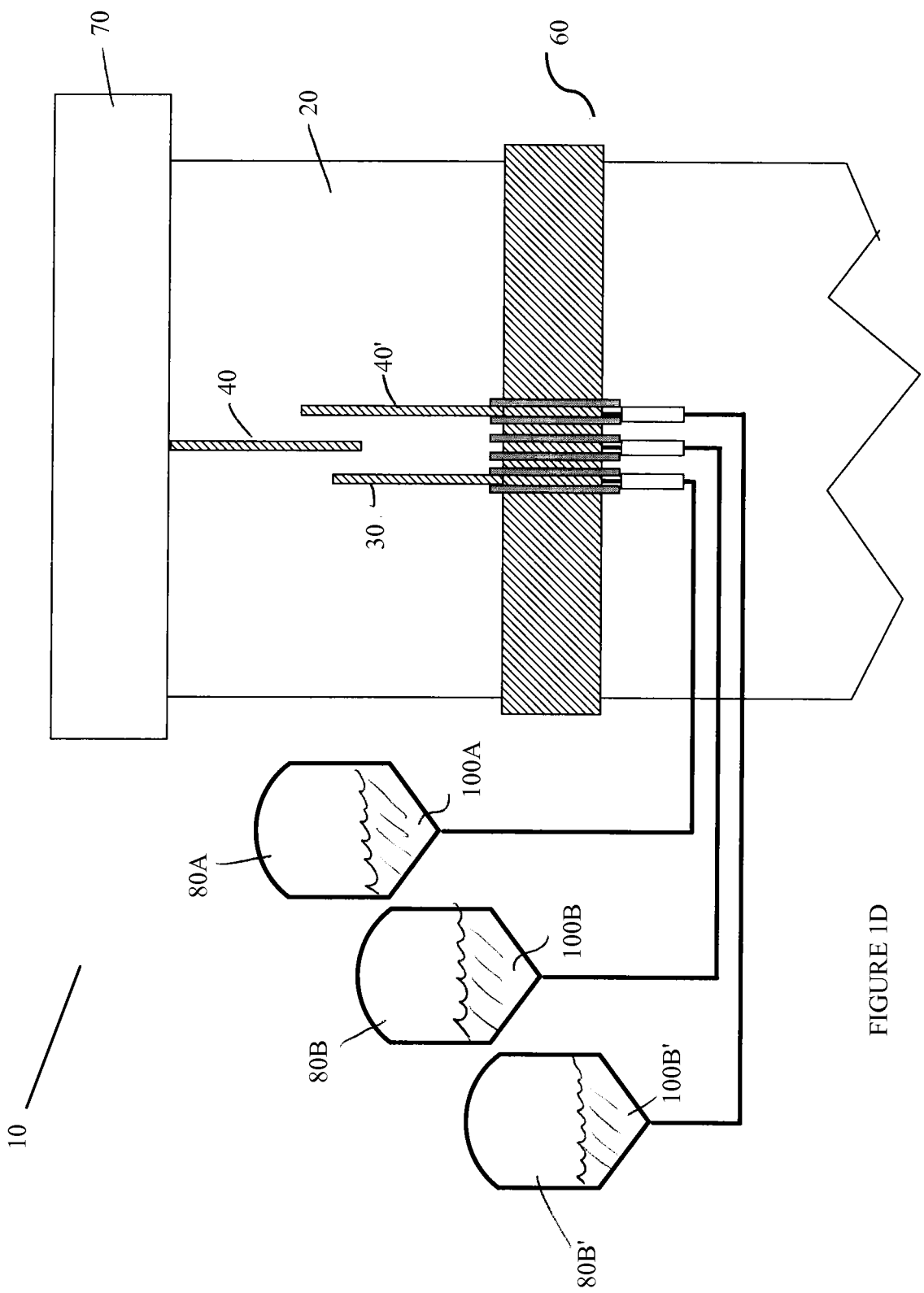

For a two-lane system (i.e., including lanes 30, 40), each lane may be substantially identical in size. The rheology of the film-forming matrix will determine the desired width of each lane, but generally, each lane should be about 20 to about 40 mm wide. The apparatus 10 may include a means for applying at least two film-forming materials (100A, 100B) to the substrate 20, including, for example, a series of coating rollers 60, a dual slot die coating head 120, and the like. Two separate batches of film forming matrix 100A, 100B are formed, each matrix including substantially identical film forming materials, including, for example, polymers, solvents, sweeteners, flavors, and the like. However, the first film-forming matrix 100A will be a surrogate with less active component than the second stage film and the second film-forming matrix 100B will include the active component(s) to be used in the desired film product. In embodiments including more than two lanes, there may be more than two batches of film forming product formed, one batch for each lane. FIGS. 1C-1D depict three lanes (30, 40, 40') formed by three batches (100A, 100B, 100B'), where batches 100B and 100B' are active-containing batches and form active-containing films in lanes 40 and 40'. Alternatively, a second batch may be used to apply the active-containing film forming material to multiple lanes during processing. Once the first batch 100A, which is a surrogate, has been used to set the processing parameters, any number of lanes may be formed with a second batch 100B.

The present invention further relates to a process for forming an active-containing film product. Once at least the first batch 100A is formed, and desirably both batches (100A, 100B) are formed, the multiple lane film forming process may begin. This embodiment begins by entering the first stage of the process. In the first stage, the equipment settings are set to initial levels, including, for example, the drying apparatus temperature, the substrate speed, and the roller gaps. The first batch 100A, which is the surrogate, is applied to the substrate 20 to form the first lane 30 of the substrate 20, and is allowed to travel through the drying apparatus 70. This first application may be performed at a large scale level, for example, about 5 to about 50 kg. The first lane 30 of film forming product is dried to the desired level to form a resulting surrogate film product, and the resulting surrogate product is tested for at least one physical properties. For example, physical properties such as thickness, moisture content, and any noticeable defects may be checked. If desired, the processing parameters may be adjusted as necessary. Typically, the processing parameters may be adjusted if one or more physical properties of the resulting surrogate film are not within a desired range of acceptable levels. For example, it may be desired that the drying temperature be adjusted, the line speed be adjusted, or the roller gaps be adjusted to prepare a thicker/thinner film product. Any of the physical characteristics of surrogate film may be tested to ensure acceptable levels are achieved.

After adjustments to the processing parameters are made as necessary, the surrogate batch continues to be fed through the apparatus, forming the resulting surrogate film with the adjusted parameters. This newly formed surrogate film may be tested for at least one physical property to ensure that the properties are within desired acceptable ranges. Again, if at least one physical property is not within the desired range, further adjustments to the processing parameters may be made as necessary. The resulting surrogate film that has been formed and adjusted may be discarded if desired, or the resulting surrogate film may be used for further studies.

Notably, at this point in the process, the majority of wasted materials include the film forming materials (i.e., polymers, solvents, sweeteners, etc). Little or no active components have been used to form any products, and thus there is minimal or no wasted active material. Again, the process may not be limited to only active components, and may be directed to other expensive or rare components if necessary. The first batch 100A is desirably void of the expensive or rare component being used.

Once the resulting surrogate film has been measured and has been determined to have all desired properties and is free of undesirable defects, the determination may be made that the processing parameters are acceptable. At this point, the method then undergoes the intermediate period, i.e., a "lane switch". During the lane switch, the apparatus 10 begins to switch from a placebo film forming stage to an active-containing film forming stage. Notably, during this lane switch period, the apparatus 10 maintains the processing levels that have been adjusted during the placebo-forming stage. Thus, the apparatus 10 will continue to run at the speed and drying temperature, will have the same roller gap width, and any other processing parameters that have been adjusted during the placebo film forming stage. In other words, during and subsequent to the lane switch period, the parameters of the apparatus 10 have already been adjusted to form a surrogate product that meets the desired properties of the resulting film.

During the lane switch period, the first batch 100A including the surrogate product stops being fed into the first lane 30, and the second batch 100B including the active-containing product begins to be fed to form the second lane 40. As discussed above, there may be more than two lanes, and the second batch 100B may be fed into multiple lanes, if desired. This begins the second stage of the process, where an active-containing film product is formed.

During the second stage, the second batch 100B, which contains the active component (or alternatively, an expensive/rare component) and any film-forming materials, is applied to the substrate 20 to form the second lane 40. Desirably, the second batch 100B is applied to the substrate 20 to form the second lane 40 through the use of coating rollers 60, which have a gap size that has been set during the first stage. Alternatively, the second batch 100B may be applied to the substrate 20 via other methods, such as extrusion. The second batch 100B is applied to the substrate 20 in the desired amount via an extrusion head or other forming mechanism. After the second lane 40 is formed, it is allowed to travel through apparatus 10 at the speed that was set during the first stage, and the drying apparatus 70 is set to a temperature that has been adjusted during the first stage. Thus, the resulting film product from the second lane 40 should have the desired properties, including thickness, uniformity, moisture content, and the like, and should be free of visible defects, such as cracking. Since the processing parameters had already been adjusted during the first stage, desirably no further adjustment is necessary for the second stage of processing, and thus minimal active-containing material should be wasted due to defective processing. Of course, it is understood that slight adjustments may be necessary due to manufacturing defects, but in general, the resulting product formed through the second stage should have all desired properties of the film. This resulting active-containing film product may be suitable for use in any way desired by the end user. For example, the resulting product may be cut into a plurality of individual dosages of substantially the same size, or the resulting film product may be stored for later use. The resulting film product desirably includes a substantially uniform amount of active component throughout the film product. Further, if the resulting product is cut into a plurality of individual dosages of substantially the same size, each individual dosage should vary in active content by no more than about 10% between each dosage.

The multiple lane process may include more than two lanes and more than one active-containing batches of film forming material. For example, the process may include three lanes and include three separate batches. The first batch, as explained above, is a surrogate batch, which is used in the first stage described above. The second batch may be a film forming batch including a first active component, which will be used to form a first active-containing film product in the second stage. The third batch may be a film forming batch including a second active component, which will be used to form a second active-containing film product in the second stage. The first and second actives may be the same or may be different. More than three active-containing batches may be used as desired to form as many active-containing products as desired.

Through the multiple lane processing method described herein, an active-containing film product may be formed having suitable and desirable properties without the need to waste a substantial amount of active materials. In fact, in desirable embodiments, the process described herein provides an active-containing film product without resulting in any wasted active components. This process thus saves not only considerable time and expense to the user, but also allows for the formation of more suitable active-containing products, especially if the actives are in limited supply. As explained above, the process is not limited to active components, but may also be used to form products including rare or expensive components. In such embodiments, the second batch (and any subsequent batches thereafter) will include the rare or expensive component(s).

In addition to the considerable savings that are achieved through the process and the reduction of wasted precious materials, the multiple lane procedure described herein also provides additional benefits. For example, typical processing uses a single-lane system to form all film products. Thus, even if a surrogate product is first formed before an active-containing product is formed; the lane would have to be completely cleaned of the surrogate solution before it can be used for the active-containing solution. In addition to adding unnecessary time to the process, this process can easily disturb the processing parameters, including, for example, the gap settings. Thus, in the process of cleaning the lane, the adjustments that have been made may be undesirably modified. In addition, local environmental conditions may change during the cleaning process, which may also affect the final, resulting active-containing film product. With a multiple lane process, the transition from surrogate film to active-containing film is achieved quickly, without the need for cleaning the lane or allowing time to pass between applications of layers.

The end result is an active-containing film that has the desired physical properties for the end product, while minimizing or altogether eliminating wasted active materials.

A number of embodiments of the invention have been described. Nevertheless, it will be understood that various modifications may be made without departing from the spirit and scope of the invention. Further, the steps described above may be modified in various ways or performed in a different order than described above, where appropriate. Accordingly, alternative embodiments are within the scope of the disclosure.

What is claimed is:

1. A method of forming an active component-containing film product in a film forming apparatus, comprising the steps of:
   a. providing a coating head configured to deposit a film forming matrix in a first lane and in a second lane onto a substrate, wherein said first lane and said second lane are offset from and substantially parallel to one another;
   b. providing a first batch of a first film forming matrix comprising at least one polymer;
   c. providing a second batch of a second film forming matrix comprising at least one polymer and an active component;
   d. applying a layer of said first batch through said coating head in said first lane and drying said first applied layer to form a resulting surrogate film;
   e. measuring said resulting surrogate film for at least one physical property;

f. optionally, adjusting at least one processing parameter and repeating steps (d) and (e) above to modify said at least one physical property; and thereafter g. applying a layer of said second batch in said second lane and drying said second applied layer to form the active component-containing film product, wherein said active component is selected from the group consisting of pharmaceuticals, pharmaceutically active agents, medicaments, drugs, neutraceuticals, cosmetic agents, biologic agents, bioeffecting substances, medicating active ingredients, medications, and combinations thereof; and wherein said surrogate film comprises less active component than said active component-containing film product or comprises no active component.

2. The method of claim 1, wherein each of said lanes comprises two parallel dams forming the sides of said lane.

3. The method of claim 1, wherein said coating head comprises at least three lanes.

4. The method of claim 1, wherein said lanes each have width of about 20 to about 40 mm.

5. The method of claim 1, wherein said first film forming matrix includes a polymer, a solvent, and no active.

6. The method of claim 1, wherein said second film forming matrix includes a polymer, a solvent and an active.

7. The method of claim 1, wherein said film forming apparatus comprises a coating roller, a movable substrate, and a drying apparatus.

8. The method of claim 7, wherein step (d) comprises the step of moving said substrate through said drying apparatus.

9. The method of claim 1, wherein said physical property includes at least one physical property selected from group consisting of film thickness, moisture content, coat weight, and combinations thereof.

10. The method of claim 1, wherein said physical property includes visible defects.

11. The method of claim 1, wherein said processing parameter comprises a parameter selected from the group consisting of roller gap size, substrate speed, drying temperature, and combinations thereof.

12. The method of claim 1, wherein said second batch includes at least 30% active by weight based on the weight of the second batch.

13. The method of claim 1, wherein said second batch is applied to said substrate at about 10 mg/cm$^2$.

14. The method of claim 1, further comprising the step of:

h. cutting said film product into a plurality of individual dosage units of the same size.

15. The method of claim 14, wherein assays of said individual dosage units have a relative standard deviation not greater than 7.8%.

* * * * *